US009877951B2

(12) United States Patent
McDevitt

(10) Patent No.: US 9,877,951 B2
(45) Date of Patent: Jan. 30, 2018

(54) METHOD FOR TREATING DEMENTIA

(71) Applicant: College of William and Mary, Williamsburg, VA (US)

(72) Inventor: Jason P. McDevitt, Williamsburg, VA (US)

(73) Assignee: College of William and Mary, Williamsburg, VA (US)

( * ) Notice: Subject to any disclaimer, the term of this patent is extended or adjusted under 35 U.S.C. 154(b) by 9 days.

(21) Appl. No.: 15/040,566

(22) Filed: Feb. 10, 2016

(65) Prior Publication Data

US 2016/0235719 A1     Aug. 18, 2016

Related U.S. Application Data

(60) Provisional application No. 62/263,031, filed on Dec. 4, 2015, provisional application No. 62/121,861, filed on Feb. 27, 2015, provisional application No. 62/118,729, filed on Feb. 20, 2015, provisional application No. 62/115,424, filed on Feb. 12, 2015.

(51) Int. Cl.
*A61K 31/42*    (2006.01)
*A61K 45/06*    (2006.01)

(52) U.S. Cl.
CPC .............. *A61K 31/42* (2013.01); *A61K 45/06* (2013.01)

(58) Field of Classification Search
CPC ................................ A61K 31/42; A61K 45/06
USPC ....................................................... 514/17.3
See application file for complete search history.

(56) References Cited

U.S. PATENT DOCUMENTS

| | | | |
|---|---|---|---|
| 5,061,721 A | 10/1991 | Cordi | |
| 6,228,875 B1 | 5/2001 | Tsai | |
| 6,420,404 B2 * | 7/2002 | Herting | A61K 31/42 514/380 |
| 7,655,655 B1 | 2/2010 | McDevitt | |
| 7,750,030 B2 | 7/2010 | Davis | |
| 7,846,913 B2 | 12/2010 | McDevitt | |
| 8,309,535 B2 | 11/2012 | McDevitt | |

OTHER PUBLICATIONS

Gottlieb et al. D-cycloserine facilitation of cognitive behavioral therapy for delusions in schizophrenia. Schizophrenia Research 131: 69-74, 2011. (Year: 2011).*
Warmus et al., "Tau-Mediated NMDA Receptor Impairment Underlies Dysfunction of a Selectively Vulnerable Network in a Mouse Model of Frontotemporal Dementia", The Journal of Neuroscience (2014), vol. 34(49), p. 16482-16495.
Schade et al., "D-Cycloserine in Neuropsychiatric Diseases: A Systematic Review", International Journal of Neuropsychopharmacology (2015), p. 1-7.
Tsai et al., "A Preliminary Study of d-Cycloserine Treatment in Alzheimer's Disease", The Journal of Neuropsychiatry and Clinical Neurosciences (1998), vol. 10(2), p. 224-226.
Tsai et al., "Improved Cognition in Alzheimer's Disease With Short-Term D-Cycloserine Treatment", American Journal of Psychiatry (1999), vol. 156(3), p. 467-469.
Laake et al., "D-cycloserine for Alzheimer's disease (Review)", Cochrane Database of Systematic Reviews (2002), Issue 2. Art No. CD003153.
Boxer et al., "Memantine in patients with frontotemporal lobardegeneration: a multicentre, randomised, double-blind, placebo-controlled trial", Lancet Neurology (2013) vol. 12, p. 149-156.
Weber et al., "Effects of D-cycloserine on extinction of learned fear to an olfactory cue", Neurobiology of Learning and Memory (2007), vol. 87, p. 476-482.
Werner-Seidler et al., "Effects of D-Cycloserine on Extinction: Consequences of Prior Exposure to Imipramine", Biological Psychiatry (2007), vol. 62, p. 1195-1197.
Khanna et al., "NMDA Antagonists and Tolerance to Drugs Affecting the Central Nervous System", CNS Drug Reviews (1999), vol. 5(2), p. 165-176.
Jensen et al., "Use of Acetylacetone to Prepare a Prodrug of Cycloserine", Journal of Medicinal Chemistry (1980), vol. 23, p. 6-8.
Parnas et al., "Effects of multiple exposures to D-cycloserine on extinction of conditioned fear in rats", Neurobiology of Learning and Memory (2005), vol. 83, p. 224-231.
Ho et al., "Effects of d-cycloserine on MPTP-induced behavioral and neurological changes: Potential for treatment of Parkinson's disease dementia", Behavioural Brain Research (2011), vol. 219, p. 280-290.
Cardarelli et al., "Frontotemporal Dementia: A Review for Primary Care Physicians", American Family Physician (2010), vol. 82(11), p. 1372-1377.
Raabe et al., "Antidepressant Interactions with the NMDA NR1-1b Subunit", Journal of Biophysics (2008), vol. 2008, Article ID 474205.
Van Berckel et al., "Behavioral and Neuroendocrine Effects of the Partial NMDA Agonist D-cycloserine in Healthy Subjects", Neuropyschopharmacology (1997), vol. 16 (5), p. 317-324.

* cited by examiner

*Primary Examiner* — Yih-Horng Shiao

(74) *Attorney, Agent, or Firm* — Jason P. McDevitt

(57) ABSTRACT

Methods are disclosed for treating dementia, including mild cognitive impairment, via administration of D-cycloserine, or a prodrug thereof, on a tolerance-inhibiting basis. Specifically, by administering D-cycloserine on a tolerance-inhibiting basis, tolerance to D-cycloserine is less likely than would occur via daily administration, enhancing benefits and reducing costs and side effects. Pharmaceutical compositions useful for the treatment of dementia are additionally disclosed.

12 Claims, No Drawings

METHOD FOR TREATING DEMENTIA

CROSS-REFERENCE TO RELATED APPLICATIONS

The present application claims priority under 35 U.S.C. § 119(e) to (i) U.S. Provisional Patent Application No. 62/263,031, filed Dec. 4, 2015, (ii) U.S. Provisional Patent Application No. 62/121,861, filed Feb. 27, 2015, (iii) U.S. Provisional Patent Application No. 62/118,729, filed Feb. 20, 2015, and (iv) U.S. Provisional Patent Application No. 62/115,424, filed Feb. 12, 2015. The disclosures of these applications are incorporated by reference herein.

STATEMENT REGARDING FEDERALLY SPONSORED RESEARCH OR DEVELOPMENT

Not applicable.

FIELD OF INVENTION

The invention relates generally to the treatment of dementia, including the early stage of dementia known as mild cognitive impairment, by administering D-cycloserine on a tolerance-inhibiting basis.

BACKGROUND

D-Cycloserine ("DCS") has long been clinically approved and used as an antibiotic to treat tuberculosis.

DCS has also been shown to improve learning and enhance memory in some situations, and has been the subject of many patents and patent applications covering neuropsychiatric disorders including Alzheimer's Disease (see, for example, Cordi, U.S. Pat. No. 5,061,721, and Tsai, U.S. Pat. No. 6,228,875), anxiety disorders (see, for example, Davis, U.S. Pat. No. 7,750,030), and depression (see McDevitt, U.S. Pat. No. 8,309,535). DCS has been widely studied in human clinical trials as a potential treatment for dementia conditions including Alzheimer's Disease, showing benefits in at least some of the clinical trials, but no significant benefit in others. For example, a multi-center, 410-patient clinical trial conducted by Searle Pharmaceuticals concluded that DCS at up to 50 mg daily dosing did not have a significant benefit for treatment of Alzheimer's Disease (Fakouhi et al., J Geriatr Psychiatry Neurol, October 1995, vol. 8, no. 4, pp. 226-230). A meta-analysis looking at numerous clinical studies with DCS and Alzheimer's Disease concluded that: "The lack of a positive effect of D-cycloserine on cognitive outcomes in controlled clinical trials with statistical power high enough to detect a clinically meaningful effect means that D-cycloserine has no place in the treatment of patients with Alzheimer's disease." (Laake et al., Cochrane Database Syst Rev. 2002; (2): CD003153) However, a study from Tsai et al. concluded that 100 mg daily administration of DCS had a positive benefit on Alzheimer's Disease (Tsai et al., Am J Psychiatry. 1999 March; 156(3): 467-9).

DCS has shown promise in animal studies for treatment of other forms of dementia. For example, based on rat studies, DCS has been suggested as a candidate for treatment of frontotemporal dementia (Warmus et al., "Tau-Mediated NMDA Receptor Impairment Underlies Dysfunction of a Selectively Vulnerable Network in a Mouse Model of Frontotemporal Dementia", The Journal of Neuroscience, 3 Dec. 2014, 34(49): 16482-16495) and also dementia related to Parkinson's Disease (Behav. Brain Res. 2011 Jun. 1; 219(2): 280-90).

While DCS is a partial agonist of the NMDA receptor, memantine is an antagonist of the NMDA receptor. Memantine is FDA-approved for treatment of Alzheimer's Disease, sold under the tradename NAMENDA® in the United States.

DCS, when administered daily for significant periods, induces physiological changes that reduce its activity. For example, Werner-Seidler and Richardson showed that the well-known ability of DCS to facilitate extinction learning is eliminated in rats if the rats have been exposed to DCS for 15 consecutive days. Moreover, antidepressants can have similar effects, and daily administration of imipramine for 15 days also blocked the ability of DCS to facilitate extinction learning (Werner-Seidler et al., "Effects of D-Cycloserine on Extinction: Consequences of Prior Exposure to Imipramine", Biological Psychiatry, Volume 62, Issue 10, 15 Nov. 2007, Pages 1195-1197). Parnas et al. (Neurobiology of Learning and Memory, 83 (2005) 224-231) showed that administering DCS to rats for five consecutive days, followed by a conventional extinction learning paradigm two days later, significantly decreased the ability of DCS to facilitate extinction. In contrast, when DCS was administered for five consecutive days, followed by a conventional extinction learning paradigm 28 days later, the ability of DCS to facilitate extinction was restored. DCS also enhances development of tolerance to other compounds, including for example ethanol (see Khanna et al., CNS Drug Reviews, Vol. 5, No. 2, pp. 165-176).

BRIEF SUMMARY OF THE INVENTION

Provided herein is a method for treatment of dementia via administration of DCS, or a suitable prodrug, on a tolerance-inhibiting basis to a human subject with dementia or mild cognitive impairment. While DCS has been shown to improve memory and learning under certain conditions, the effect has not been sufficient to justify pivotal clinical trials and the expense of drug development. Unfortunately, the human body rapidly develops tolerance to DCS, and daily administration becomes less effective. In contrast, tolerance-inhibiting administration, defined herein as administration of DCS (or a suitable prodrug thereof) on a given day, and then administered no more frequently than one additional time in the subsequent 168 hours (i.e., one week), reduces development of tolerance and preserves the benefits of DCS. Surprisingly, the benefits of tolerance-inhibiting administration of DCS or a suitable DCS prodrug for dementia can over the long term (e.g., six months) exceed the benefits of chronic daily administration, while reducing drug-related costs and side effects. The benefits may be particularly efficacious for the early stage of dementia known as mild cognitive impairment. Other dementia conditions that can be treated according to the methods described herein include Alzheimer's Disease, vascular dementia, dementia with Lewy bodies, dementia related to Parkinson's Disease, and frontotemporal dementia.

According to the methods herein, DCS is administered at a dose between about 50 mg up to 250 mg, e.g., at 50 mg, 75 mg, 100 mg, 125 mg, 250 mg, or other dosages between 50 mg and 250 mg. Alternatively, if a suitable DCS prodrug is administered, it is administered at a dosage that would provide an equivalent concentration of DCS in the body. For example, if the acetylacetone prodrug of DCS is used, it should be administered at a dose between about 90 mg up to 450 mg, e.g., at 90 mg, 100 mg, 150 mg, 200 mg, 250 mg, 300 mg, 400 mg, 450 mg, or dosages between 90 mg and 450 mg. This DCS prodrug, (R)-4-[(1-methyl-3-oxo-1-butenyl)-amino]-3-isoxazolidinone, is particularly useful, providing enhanced stability relative to DCS without compromising activity.

In some embodiments, tolerance-inhibiting administration of DCS, or suitable prodrug, to subjects with dementia or mild cognitive impairment is paired with a requirement for subjects not to be administered either a selective serotonin reuptake inhibitor (SSRI) or tricycylic antidepressant (TCA) within one week prior to or subsequent to administration of DCS or suitable prodrug. Specifically, SSRIs or TCAs can interfere with the beneficial effects of DCS. While antidepressants such as SSRIs or TCAs are sometimes used for patients with dementia, including mild cognitive impairment, the combination of these antidepressants with DCS (or suitable prodrug) is counterproductive.

In some embodiments, DCS or a suitable prodrug is intentionally administered to a subject with dementia within two hours of onset of the subject's night-time sleeping period. Consequently, DCS will be at therapeutically effective levels during the subject's sleep, which can be particularly beneficial for neuronal plasticity. Generally, a subject treated according this method would self-administer a therapeutically effective amount of DCS or suitable prodrug just prior to an attempt to fall asleep for the night.

In some embodiments, DCS or a suitable prodrug is administered on a tolerance-inhibiting basis in conjunction with other drugs administered daily for treatment of dementia, including but not limited to donezepil, galantamine, memantine, rivastigmine, and tacrine. DCS can be particularly beneficial when paired with cholinesterase inhibitors such as donezepil, galantamine, rivastigmine, and tacrine, as the mechanisms of action can be complementary.

BRIEF DESCRIPTION OF THE SEVERAL
VIEWS OF THE DRAWINGS

Not applicable.

DETAILED DESCRIPTION OF THE
INVENTION

Described herein are methods for treatment of dementia, including mild cognitive impairment, by tolerance-inhibiting administration of DCS to subjects with dementia or mild cognitive impairment, said DCS administered at a dose of between about 50 mg and 250 mg or at a dose of a prodrug that yields comparable concentrations of DCS in the body.

In some embodiments, DCS is administered to subjects in need thereof on a pre-sleep basis, i.e., within two hours of the subject's intended nightly sleep period. Accordingly, serum levels of DCS in the subject will at certain times during the night be sufficiently high to be therapeutically effective, and these timely serum levels can be achieved using the disclosed methods for administering DCS within two hours of the onset of a subject's nightly sleep period. As contemplated herein, a subject's nightly sleep period is the portion of the 24-hour daily cycle when the subject sleeps, or intends to sleep, for the longest period. For most individuals, this nightly sleep period takes place during the evening hours. Sleep is the natural state of bodily rest in animals, and includes rapid eye movement (REM) sleep and non-rapid eye movement (NREM) sleep. Human sleep proceeds in cycles of REM and NREM sleep (there are multiple stages of NREM sleep), with a typical full sleep cycle lasting between 90 minutes and 120 minutes. Accordingly, in a nightly sleep period, a subject may complete several sleep cycles. According to the methods of the invention, pre-sleep administration of DCS will typically yield therapeutically effective serum levels of DCS through at least a significant portion of the nightly sleep period, including multiple cycles of REM sleep and NREM sleep.

D-cycloserine, or DCS, refers to the chemical D-cycloserine (CA Index Name: 3-Isoxazolidinone, 4-amino-, (4R)- (9CI); CAS Registry No. 68-41-7), or pharmaceutically acceptable salts thereof, or pharmaceutically acceptable prodrugs thereof. DCS is an FDA (United States Food and Drug Administration)-approved drug for treatment of tuberculosis, and is sold in the United States under the trade name Seromycin®. DCS is a structural analog of D-alanine, and is a broad-spectrum antibiotic produced by some strains of *Streptomyces orchidaceus* and *S. garphalus*. DCS has antibiotic activity in vitro against growth phase Gram-negative bacteria such as *Escherichia coli*, some strains of *Staphylococcus aureus*, and Chlamydia species, among others. The minimum inhibitory concentrations (MIC) in vitro for typical Mycobacterium tuberculosis strains range from about 6-25 µg/mL.

For the treatment of tuberculosis, DCS is generally dosed at 500-1000 mg/day divided twice daily (PDR 1997) with chronic treatment. At a dose of 500 mg/day, serum concentrations of 25-30 µg/mL are generally maintained. Administration of oral capsules of D-cycloserine typically results in peak serum concentrations occurring within 3-8 hours after dosing, with a half-life of 10 hours and primarily renal excretion.

At these typical doses for the treatment of tuberculosis, DCS can give rise to significant neurological side effects in treated subjects. Recorded side effects on chronic dosing schedules (wherein subjects were generally chronically ill with tuberculosis) include drowsiness, depression, headache, confusion, tremor, vertigo, and memory difficulties, paresthesias, and seizure.

As contemplated herein, a therapeutically effective amount of DCS for treatment of dementia is lower than the amounts typically used for the treatment of tuberculosis. A "therapeutically effective amount" or "therapeutically effective dose" of the pharmacologic agent is an amount of the pharmacologic agent that typically results in an improved treatment, e.g., a greater therapeutic benefit, or a therapeutic benefit for a longer time, relative to that observed in the absence of administering the pharmacologic agent.

In some embodiments, a therapeutically effective amount of DCS used in the disclosed methods relates to a sub-antimicrobial dose of DCS. A sub-antimicrobial dose refers to a dose of DCS that is less than or equal to 2 mg DCS per kg body weight of the subject (i.e., less than or equal to 2 mg/kg), and preferably greater than about 0.2 mg/kg (this lower limit is believed to be needed to maintain efficacy for facilitation of extinction). When administered to a subject, sub-antimicrobial doses of DCS achieve peak serum concentrations in the subject of less than or equal to about 5 µg/mL, although there is substantial variability between subjects. At these low concentrations of DCS, the drug no longer kills most microorganisms, including those that are ordinarily susceptible to higher DCS concentrations typically reached in the body when DCS is used to treat tuberculosis (i.e., based on dosing of 500 mg or 1000 mg per day).

All microorganisms do not have the same susceptibility to DCS. Accordingly, while it is possible that a sub-antimicrobial dose of DCS can still kill a small subset of microorganisms, sub-antimicrobial doses of DCS generally will not have a significant antimicrobial effect in the body. When administered to adult human subjects, a sub-antimicrobial dose of DCS generally comprises a drug formulation (e.g., pill, capsule, tablet) of DCS containing DCS in an amount equal to or less than 100 mg, preferably less than 80 mg DCS (e.g., about 5 mg to about 100 mg, or about 10 mg to about 100 mg, or even about 10 mg to about 80 mg) to provide a greater margin between the concentration of DCS and the minimum inhibitory concentration (MIC) of DCS against microorganisms active in a subject's body.

When administered to a subject as disclosed herein, a therapeutically effective serum concentration of DCS is achieved within for example 30 minutes, 1 hour, or even 2 hours after administration.

Serum concentration levels of DCS in subjects to whom DCS is administered are a function of numerous factors, including body weight, metabolism, and the amount of drug ingested. The timing of administration and the therapeutically effective dose of DCS in a given subject will depend on the severity of symptoms, in addition to the age, sex, and size of the subject being treated, among other variables.

DCS is a partial agonist of the NMDA receptor, and doses of greater than 250 mg can reduce transmission at the NMDA receptor (i.e., serve as functional antagonists of the receptor), so DCS is administered at doses of 250 mg or less. In order to achieve sufficient concentrations for efficacy, doses of at least 50 mg are needed. DCS can dimerize upon storage, particularly in the presence of water vapor, and so it can be advantageous to use a prodrug that has enhanced stability during storage and then is transformed to DCS in the body. A particularly suitable prodrug is the condensation product of DCS and acetylacetone, specifically (R)-4-[(1-methyl-3-oxo-1-butenyl)-amino]-3-isoxazolidinone (see Jensen et al., "Use of acetylacetone to prepare a prodrug of cycloserine", *Journal of Medicinal Chemistry* (1980) 23 (1), 6-8.)

Dementia is not a specific disease, but rather an overall term that describes a wide range of symptoms associated with a decline in memory or other skills (e.g., communication and language, ability to focus and pay attention, reasoning and judgment, visual perceptions) severe enough to reduce a person's ability to perform everyday activities. Dementia can be split into two broad categories—the cortical dementias and the subcortical dementias—based on which part of the brain is affected. Alzheimer's disease accounts for the majority of dementia cases, but there are many other forms of dementia, including but not limited to vascular dementia, frontotemporal dementia, dementia with Lewy bodies, and dementia associated with Parkinson's Disease.

Alzheimer's Disease is the most common form of dementia, and is widely used as a general term for memory loss and other intellectual abilities serious enough to interfere with daily life. Alzheimer's disease accounts for 60 to 80 percent of dementia cases. Alzheimer's Disease is a type of dementia that causes problems with memory, thinking and behavior. Symptoms usually develop slowly and get worse over time, becoming severe enough to interfere with daily tasks.

Vascular dementia is a decline in thinking skills caused by conditions that block or reduce blood flow to the brain, thereby depriving brain cells of vital oxygen and nutrients. In vascular dementia, changes in thinking skills sometimes occur suddenly as a result of strokes that block major brain blood vessels. Thinking problems also may begin as mild changes that worsen gradually as a result of multiple minor strokes or other conditions that affect smaller blood vessels, leading to cumulative damage. The term vascular cognitive impairment is sometimes used instead of the term "vascular dementia".

Frontotemporal dementia (FTD) is a common form of dementia in humans under the age of 65 years. Variants of FTD include but are not limited to behavioral variant FTD, semantic dementia, and progressive nonfluent aphasia. Behavioral and language manifestations are core features of FTD, and patients have relatively preserved memory, which differs from Alzheimer disease. Common behavioral features include loss of insight, social inappropriateness, and emotional blunting, while common language features are loss of comprehension and object knowledge (semantic dementia), and nonfluent and hesitant speech (progressive nonfluent aphasia). A careful history and physical examination, supplemented as needed by magnetic resonance imaging, is useful in distinguishing FTD from other common forms of dementia, including Alzheimer's disease, dementia with Lewy bodies, and vascular dementia. FTD is characterized by progressive neuronal loss predominantly involving the frontal and/or temporal lobes. Brain atrophy in the frontal and/or temporal lobes is a pathologic feature of the FTD disorders Although no cure for FTD exists, and there are no drugs approved by FDA specifically for FTD, symptom management with selective serotonin reuptake inhibitors, antipsychotics, and galantamine has been shown to be beneficial (see Cardarelli et al., "Frontotemporal Dementia: A Review for Primary Care Physicians", *Am. Fam. Physician.* 2010 Dec. 1; 82(11): 1372-1377).

Mild cognitive impairment, also known as incipient dementia or age-associated memory impairment, is a brain function syndrome involving the onset and evolution of cognitive impairments beyond those expected based on the age and education of the individual, but which have not yet risen to a sufficient level to significantly interfere with the daily activities of an afflicted individual. It frequently occurs as a transitional stage between the expected cognitive decline of normal aging and the more serious decline of dementia. It can present as problems with memory, language, thinking and judgment that are greater than normal age-related changes. Mild cognitive impairment increases one's likelihood of later progressing to more advanced dementia such as Alzheimer's Disease, but this progression is not a certainty. Herein, mild cognitive impairment is defined as a dementia, although some prior art references refer to it as a pre-dementia.

The methods of the invention are particularly useful for treatment of mild cognitive impairment. The neuroplasticity enhancements of DCS, coupled with the excellent safety profile of DCS when administered on a tolerance-inhibiting basis, are particularly suitable for long-term treatment to prevent or reduce the rate of cognitive decline. DOS offers the possibility of reversing or slowing cognitive decline, and the methods described herein can do so with minimal side effects. Unlike other proposed treatments which, for example, are intended to block biological pathways around the dock, the methods described herein provide a pulsed, modest adjustment, which is particularly suitable for long-term treatment of mild cognitive impairment. These methods can be particularly beneficial when DCS is administered on a pre-sleep basis as defined herein. It would be a great success to identify a method of treatment that, for example, significantly delayed the progress of mild cognitive impairment to a full-blown dementia, or significantly reduced the annual conversion rate as measured in a clinical trial without introducing deleterious side effects. For every year that the onset of Alzheimer's dementia can be delayed, there is an approximately 10% reduction in the prevalence of this disease according to the National Institute of Aging.

According to the methods of the invention for treating dementia, DCS is administered on a tolerance-inhibiting basis. Tolerance-inhibiting administration of DCS to a subject means that the DCS is not dosed on a chronic, daily basis, but rather is administered on an intermittent basis. Specifically, in any given 7-day cycle, DCS is administered to a human subject on the first day, and then is administered no more than one additional time within the first week. In one embodiment, DCS could be administered daily for two days, then not administered for the next 5 days, before starting a subsequent cycle. In another embodiment, DCS is administered on a once-weekly basis. In another embodiment, DCS is administered every Saturday and Sunday, but not on weekdays. In another embodiment, DCS is administered every 3.5 days for 10 years. Each 7-day cycle does not require consistent treatment. For example, DCS could be administered twice-weekly for the first two-week cycle, then once-weekly for four weeks, then two days in a row followed by 10 days off, then every fifth day. Many other embodiments can be contemplated.

In all such embodiments, the key feature is that the efficacy of the DCS treatment is maintained because the subject does not develop significant tolerance to DCS. Development of tolerance to a drug can depend on many different factors, and tolerance to different effects of a drug do not necessarily take the same time, and instead can vary enormously (Christiaan H. Vinkers and Berend Olivier, "Mechanisms Underlying Tolerance after Long-Term Benzodiazepine Use: A Future for Subtype-Selective Receptor Modulators?", Advances in Pharmacological Sciences, Vol. 2012, Article ID 416864, 19 pages, 2012. doi: 10.1155/2012/416864). NMDA receptors are up-regulated in the brain as a result of benzodiazepine tolerance.

To avoid developing significant tolerance to DCS for treatment of dementia: (i) blood concentration levels of DCS should be below 3 µg/ml at least 75% of the time over a one month period, (ii) blood concentration levels of DCS should be less than 10% of the peak DCS blood concentration at least 50% of the time during said one month period, and (iii) the minimum DCS blood concentration during the one month period, subsequent to the first administration of DCS during said one month period, should be less than 1% of the peak DCS blood concentration during said one month period. These conditions are met when DCS is administered on a tolerance-inhibiting basis according to the methods taught herein.

By administering DCS on a tolerance-inhibiting basis, rather than daily administration at the same dosage, development of drug tolerance is reduced, and down-regulation of the NMDA receptors is less likely. This is important for long-term treatment with DCS, as might be appropriate for treatment of dementia, including, for example, treatment of mild cognitive impairment or treatment of FTD.

It is contemplated that other agents may be also administered before, during, or after the administration of DCS. For example, a B vitamin, such as one or more of the B-complex vitamins, can be administered to a subject in addition to DCS, as part of the contemplated methods. A B-complex vitamin includes thiamine (B1), riboflavin (B2), niacin (B3), pyridoxine (B6), folic acid (B9), cyanocobalamin (B12), pantothenic acid (B5) and biotin. For example, pyridoxine can be additionally administered at up to ten times the dosage of DCS. In an embodiment, the DCS for administration as contemplated herein is provided in a composition that includes a B-complex vitamin, e.g., pyridoxine, as a tablet or other composition that includes for example 50 mg DCS and 1.5 mg pyridoxine. DCS has been reported to reduce the levels of certain important chemicals in the blood of subjects, including calcium, folic acid, magnesium, vitamin K, and vitamin B6 and vitamin B12. In another embodiment, a DCS prodrug is formulated along with a B-complex vitamin. For example, a pharmaceutical composition comprising between 90 and 450 mg (R)-4-[(1-methyl-3-oxo-1-butenyl)-amino]-3-isoxazolidinone, along with between 5 mg and 50 mg B-complex vitamins. For example, in one embodiment, a pharmaceutical composition useful for treating dementia comprises 200 mg (R)-4-[(1-methyl-3-oxo-1-butenyl)-amino]-3-isoxazolidinone, 1.0 mg thiamine, 15 mg niacin, 6.0 mg pantothenic acid, 1.4 mg pyridoxine, 2.5 mcg vitamin B-12, 50 mcg biotin, and 200 mcg folic acid.

Additionally, tolerance-inhibiting DCS administration for treatment of dementia can also be combined with administration of other medications on a daily or non-daily basis for treatment of dementia. For example, DCS can administered on a tolerance-inhibiting basis in conjunction with other drugs administered daily for treatment of dementia, including but not limited to donezepil, galantamine, memantine, rivastigmine, and tacrine. In one exemplary embodiment, DCS is administered on a tolerance-inhibiting basis while donezepil is administered on a daily basis.

Selective serotonin reuptake inhibitors ("SSRIs", e.g., fluvoxamine, sertraline, citalopram, escitalopram, paroxetine) and tricyclic antidepressants ("TCAs", e.g., imipramine, desipramine, nortriptyline, chloripramine) are fairly widely used to treat FTD, and widely used to treat co-morbid conditions such as depression, and also used to treat patients with FTD or mild cognitive impairment (or other dementia) who have been misdiagnosed as having anxiety disorders. Unfortunately, both TCAs and SSRIs can interfere with the effects of DCS by inducing conformational changes in the NMDA-receptor subunit to which D-cycloserine binds, thereby modulating the effects of DCS treatment (Raabe, R., and Gentile, L. "Antidepressant Interactions with the NMDA NR1-1b Subunit." *Journal of Biophysics* 2008 (2008): 474205). Accordingly, in some embodiments of the invention, DCS is administered to subjects diagnosed with dementia or mild cognitive impairment provided (i) neither SSRIs nor TCAs have been administered to the subject within a week prior to DCS administration, and (ii) neither SSRIs nor TCAs are administered to the subject within a week following DCS administration, irrespective of the duration of the DCS treatment, e.g., whether DCS is administered for 2 weeks, 2 months, or 2 years.

In one exemplary embodiment, a subject suffering from Alzheimer's Disease self-administers 250 mg DCS on a weekly basis. In another embodiment, a subject suffering from Alzheimer's Disease self-administers 200 mg of the DCS prodrug (R)-4-[(1-methyl-3-oxo-1-butenyl)-amino]-3-isoxazolidinone on a once-weekly basis.

In one exemplary embodiment, a subject afflicted with mild cognitive impairment self-administers 125 mg DCS on a twice-weekly basis. In another embodiment, a subject afflicted with mild cognitive impairment self-administers 150 mg of the DCS prodrug (R)-4-[(1-methyl-3-oxo-1-butenyl)-amino]-3-isoxazolidinone on a once-weekly basis. In another embodiment, a subject afflicted with mild cognitive impairment self-administers 200 mg of the DCS prodrug (R)-4-[(1-methyl-3-oxo-1-butenyl)-amino]-3-isoxazolidinone twice weekly on a pre-sleep basis.

In one exemplary embodiment, a subject afflicted with dementia is administered 50 mg DCS every four days on a pre-sleep basis.

In one exemplary embodiment, a subject suffering from FTD is administered 100 mg DCS on a twice-weekly basis for 5 years.

In one exemplary embodiment, a subject suffering from FTD discontinues daily SSRI administration, waits one week, and then is administered 125 mg DCS on a pre-sleep basis, once per week, for 2 years.

In one exemplary embodiment, a subject suffering from FTD is administered 100 mg DCS on approximately a weekly basis for 5 years.

In one exemplary embodiment, a subject suffering from FTD is administered 75 mg DCS every four days for 5 years. The DCS is administered in an ordered package wherein a pill is taken every day, and for each DCS pill, the next three sequential pills do not contain any active ingredient. An analogous sequential package can be used for other spacing (e.g., every four days, or weekly).

In one planned exemplary embodiment, a double-blind, placebo-controlled clinical trial is conducted with the following parameters. 300 subjects diagnosed with FTD are enrolled and split into a control group (receiving placebo pill) and a treatment group (receiving DCS 75 mg capsules). Subjects take one pill (either placebo or DCS) every week for 26 weeks. Half of the subjects in each group are instructed to take their pill in the morning, and half are instructed to take their pill on a pre-sleep basis. Primary outcomes include change from baseline on Frontotemporal Dementia Rating Scale (FRS), change in Neuropsychiatric Inventory (NPI) [Time Frame: 26 weeks, NPI is a 12-domain caregiver assessment of behavioral disturbances occurring in dementia: delusions, hallucinations, agitation/aggression, depression/dysphoria, anxiety, elation/euphoria, apathy/indifference, disinhibition, irritability/lability, motor disturbance, appetite/eating, nighttime behavior] and Clinical Global Impression of Change (CGIC) [Time Frame: 26 Weeks, a 7-point scale, using a range of responses from 1 (very much improved) through 7 (very much worse), wherein the clinician compares the participant's current condition to the condition at admission to the project]. Secondary outcomes include, for example, metabolic activity in frontal and temporal lobe and change from baseline on Addenbrooke's Cognitive Examination-III (ACE-III). The pool of subjects concurrently taking SSRIs will be compared to the subjects not taking SSRIs.

Formulations

Pharmaceutical compositions contemplated by the methods of the invention may be formulated and administered to a subject for treatment of various medical conditions as described below.

The invention encompasses the preparation and use of pharmaceutical compositions comprising DCS or a suitable DCS prodrug as an active ingredient useful for treatment of dementia. Such pharmaceutical compositions may consist of DCS alone, in any form suitable for administration to a subject, a DCS prodrug in any form suitable for administration to the subject, or the pharmaceutical composition may comprise DCS or DCS prodrug and one or more pharmaceutically acceptable carriers, one or more additional ingredients, or some combination of these. The active ingredient(s) may be present in the pharmaceutical composition in the form of a physiologically acceptable ester or salt, such as in combination with a physiologically acceptable cation or anion, as is well known in the art.

In one embodiment, a pharmaceutical composition is provided of the DCS prodrug (R)-4-[(1-methyl-3-oxo-1-butenyl)-amino]-3-isoxazolidinone. Such compositions are useful for the treatment of demenia, provided in suitable dosage forms having between about 90 mg and 450 mg (R)-4-[(1-methyl-3-oxo-1-butenyl)-amino]-3-isoxazolidinone.

As used herein, the term "pharmaceutically acceptable carrier" means a chemical composition with which the active ingredient may be combined and which, following the combination, can be used to administer the active ingredient to a subject.

As used herein, the term "physiologically acceptable" ester or salt means an ester or salt form of the active ingredient which is compatible with any other ingredients of the pharmaceutical composition, which is not deleterious to the subject to which the composition is to be administered.

Subject compositions may be suitable for oral, nasal, topical (including buccal and sublingual), rectal, vaginal, aerosol and/or parenteral administration. The formulations may conveniently be presented in unit dosage form and may be prepared by any methods well known in the art of pharmacy. The amount of composition that may be combined with a carrier material to produce a single dose varies depending upon the subject being treated, and the particular mode of administration. The relative amounts of the active ingredient, the pharmaceutically acceptable carrier, and any additional ingredients in a pharmaceutical composition of the invention may vary, depending upon the identity, size, and condition of the subject treated and further depending upon the route by which the composition is to be administered. By way of example, the composition may comprise between 0.01% and 100% (w/w) active ingredient.

Formulations of the present invention may be administered parenterally as injections (intravenous, intramuscular or subcutaneous), or as drop infusion preparations.

Pharmaceutical compositions of this invention suitable for parenteral administration comprise a subject composition in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents The terms "parenteral administration" and "administered parenterally" are art-recognized and refer to modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intra-articulare, subcapsular, subarachnoid, intraspinal, and intrasternal injection and infusion.

Pharmaceutical compositions that are useful in the methods of the invention may be prepared, packaged, or sold in formulations suitable for oral, rectal, vaginal, intravenous, parenteral, topical, pulmonary, intranasal, buccal, sublingual, ophthalmic, intrathecal or another route of administration.

A formulation of a pharmaceutical composition of the invention suitable for oral administration may be prepared, packaged, or sold in the form of a discrete solid dose unit including, but not limited to, a tablet, a hard or soft capsule, a cachet, a troche, or a lozenge, each containing a predetermined amount of the active ingredient. Other formulations suitable for oral administration include, but are not limited to, a powdered or granular formulation, an aqueous or oily suspension, an aqueous or oily solution, or an emulsion. As used herein, an "oily" liquid is one which comprises a carbon-containing liquid molecule and which exhibits a less polar character than water.

A tablet comprising the active ingredient may, for example, be made by compressing or molding the active ingredient, optionally with one or more additional ingredients. Compressed tablets may be prepared by compressing, in a suitable device, the active ingredient in a free-flowing form such as a powder or granular preparation, optionally mixed with one or more of a binder, a lubricant, an excipient, a surface active agent, and a dispersing agent. Molded tablets may be made by molding, in a suitable device, a mixture of the active ingredient, a pharmaceutically acceptable carrier, and at least sufficient liquid to moisten the mixture. Pharmaceutically acceptable excipients used in the manufacture of tablets include, but are not limited to, inert diluents, granulating and disintegrating agents, binding agents, and lubricating agents. Known dispersing agents include, but are not limited to, potato starch and sodium starch glycolate. Known surface active agents include, but are not limited to, sodium lauryl sulphate. Known diluents include, but are not limited to, calcium carbonate, sodium carbonate, lactose, microcrystalline cellulose, calcium phosphate, calcium hydrogen phosphate, and sodium phosphate. Known granulating and disintegrating agents include, but are not limited to, corn starch and alginic acid. Known binding agents include, but are not limited to, gelatin, acacia, pre-gelatinized maize starch, polyvinylpyrrolidone, and hydroxypropyl methylcellulose. Known lubricating agents include, but are not limited to, magnesium stearate, stearic acid, silica, and talc.

Hard capsules comprising the active ingredient may be made using a physiologically degradable composition, such as gelatin. Such hard capsules comprise the active ingredient, and may further comprise additional ingredients including, for example, an inert solid diluent such as calcium carbonate, calcium phosphate, or kaolin.

Soft gelatin capsules comprising the active ingredient may be made using a physiologically degradable composition, such as gelatin. Such soft capsules comprise the active ingredient, which may be mixed with water or an oil medium such as peanut oil, liquid paraffin, or olive oil.

Liquid formulations of a pharmaceutical composition of the invention which are suitable for oral administration may be prepared, packaged, and sold either in liquid form or in the form of a dry product intended for reconstitution with water or another suitable vehicle prior to use.

Liquid suspensions may be prepared using conventional methods to achieve suspension of the active ingredient in an aqueous or oily vehicle. Aqueous vehicles include, for example, water and isotonic saline. Oily vehicles include, for example, almond oil, oily esters, ethyl alcohol, vegetable oils such as arachis, olive, sesame, or coconut oil, fractionated vegetable oils, and mineral oils such as liquid paraffin. Liquid suspensions may further comprise one or more additional ingredients including, but not limited to, suspending agents, dispersing or wetting agents, emulsifying agents, demulcents, preservatives, buffers, salts, flavorings, coloring agents, and sweetening agents. Oily suspensions may further comprise a thickening agent. Known suspending agents include, but are not limited to, sorbitol syrup, hydrogenated edible fats, sodium alginate, polyvinylpyrrolidone, gum tragacanth, gum acacia, and cellulose derivatives such as sodium carboxymethylcellulose, methylcellulose, hydroxypropylmethylcellulose. Known dispersing or wetting agents include, but are not limited to, naturally-occurring phosphatides such as lecithin, as well as condensation products of an alkylene oxide with either: a fatty acid, a long chain aliphatic alcohol, a partial ester derived from a fatty acid and a hexitol, or a partial ester derived from a fatty acid and a hexitol anhydride (e.g. polyoxyethylene stearate, heptadecaethyleneoxycetanol, polyoxyethylene sorbitol monooleate, and polyoxyethylene sorbitan monooleate, respectively). Known emulsifying agents include, but are not limited to, lecithin and acacia. Known preservatives include, but are not limited to, methyl, ethyl, or n-propyl-para-hydroxybenzoates, ascorbic acid, and sorbic acid. Known sweetening agents include, for example, glycerol, propylene glycol, sorbitol, sucrose, and saccharin. Known thickening agents for oily suspensions include, for example, beeswax, hard paraffin, and cetyl alcohol.

Liquid solutions of the active ingredient in aqueous or oily solvents may be prepared in substantially the same manner as liquid suspensions, the primary difference being that the active ingredient is dissolved, rather than suspended in the solvent. Liquid solutions of the pharmaceutical composition of the invention may comprise each of the components described with regard to liquid suspensions, it being understood that suspending agents will not necessarily aid dissolution of the active ingredient in the solvent. Aqueous solvents include, for example, water and isotonic saline. Oily solvents include, for example, almond oil, oily esters, ethyl alcohol, vegetable oils such as arachis, olive, sesame, or coconut oil, fractionated vegetable oils, and mineral oils such as liquid paraffin.

Powdered and granular formulations of a pharmaceutical preparation of the invention may be prepared using known methods. Such formulations may be administered directly to a subject, used, for example, to form tablets, to fill capsules, or to prepare an aqueous or oily suspension or solution by addition of an aqueous or oily vehicle thereto. Each of these formulations may further comprise one or more of dispersing or wetting agent, a suspending agent, and a preservative. Additional excipients, such as fillers and sweetening, flavoring, or coloring agents, may also be included in these formulations.

A pharmaceutical composition of the invention may also be prepared, packaged, or sold in the form of oil-in-water emulsion or a water-in-oil emulsion. The oily phase may be a vegetable oil such as olive or arachis oil, a mineral oil such as liquid paraffin, or a combination of these. Such compositions may further comprise one or more emulsifying agents such as naturally occurring gums such as gum acacia or gum tragacanth, naturally-occurring phosphatides such as soybean or lecithin phosphatide, esters or partial esters derived from combinations of fatty acids and hexitol anhydrides such as sorbitan monooleate, and condensation products of such partial esters with ethylene oxide such as polyoxyethylene sorbitan monooleate. These emulsions may also contain additional ingredients including, for example, sweetening or flavoring agents.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit. In one packaging embodiment, a suitable multi-dose unit is a blister-pack having between four and twenty doses of DCS. For example, a 10-pack of DCS capsules may be suitably prescribed to a subject.

In another embodiment, particularly useful for subjects with forgetfulness, a package is provided containing an ordered arrangement of DCS along with a majority pills having no active ingredients, wherein one dose is administered each day in a prescribed sequence. While the same number of DCS doses will be administered over the course of, for example, 30 days or 90 days, the relative likelihood of a subject forgetting to take a drug administered once-weekly is greater than the likelihood of forgetting to take a drug administered daily.

In other embodiments, pharmaceutical compositions of DCS and one or more drugs administered for treatment of dementia selected from the group consisting of donepezil, rivastigmine, galantamine, and memantine. In one embodiment, a package is provided containing an ordered arrangement of pills containing both DCS and donepezil, along with a majority pills having donepezil but not DCS, wherein one dose is administered each day in a prescribed sequence.

INCORPORATION BY REFERENCE

All publications, patents, and patent applications cited herein are hereby expressly incorporated by reference in their entirety and for all purposes to the same extent as if each was so individually denoted.

EQUIVALENTS

While specific embodiments of the subject invention have been discussed, the above specification is illustrative and not restrictive. Many variations of the invention will become apparent to those skilled in the art upon review of this specification. Contemplated equivalents of the methods of treating anxiety related disorders disclosed here include administering fast acting compositions which otherwise correspond thereto, and which have the same general properties thereof, wherein one or more simple variations of substituents or components are made which do not adversely affect the characteristics of the methods and compositions of interest. The full scope of the invention should be determined by reference to the claims, along with their full scope of equivalents, and the specification, along with such variations.

The articles "a" and "an" are used herein to refer to one or to more than one (i.e. to at least one) of the grammatical object of the article. By way of example, "an element" means one element or more than one element.

Any ranges cited herein are inclusive, e.g., "between about 50 mg and 250 mg" includes compositions of 50 mg and 250 mg.

I claim:

1. A tolerance-inhibiting administration method for treating dementia consisting of the sequential steps of:
   (A) administering to a subject in need thereof a first-scheduled therapeutically effective dose of D-cycloserine, or a pharmacologically effective prodrug thereof;
   (B) during the next one week, administering to said subject no more than one optional therapeutically effective dose of D-cycloserine, or pharmacologically effective prodrug thereof;
   (C) after at least one week has elapsed since said administering of said first-scheduled therapeutically effective dose, administering to said subject a second-scheduled therapeutically effective dose of D-cycloserine, or pharmacologically effective prodrug thereof; and
   (D) during the next one week, administering to said subject no more than one optional therapeutically effective dose of D-cycloserine or pharmacologically effective prodrug thereof,
   wherein said dementia is selected from the group consisting of mild cognitive impairment, Alzheimer's Disease, vascular dementia, dementia with Lewy bodies, dementia related to Parkinson's Disease, and frontotemporal dementia; and
   wherein said D-cycloserine is administered at a dose of between about 50 mg and about 250 mg, or said pharmaceutically effective prodrug thereof is administered at a dose of between about 90 mg and about 450 mg.

2. The method of claim 1, wherein said pharmacologically effective prodrug thereof is (R)-4-[(1-methyl-3-oxo-1-butenyl)-amino]-3-isoxazolidinone.

3. The method of claim 1, wherein said dementia is mild cognitive impairment.

4. The method of claim 1, wherein said dementia is selected from the group consisting of Alzheimer's Disease, vascular dementia, dementia with Lewy bodies, dementia related to Parkinson's Disease, and frontotemporal dementia.

5. The method of claim 1, wherein said D-cycloserine is administered on a pre-sleep basis.

6. The method of claim 1, wherein said subject is not administered an antidepressant drug compound selected from the group consisting of a selective serotonin reuptake inhibitor and a tricyclic antidepressant within one week of any of said administrations of D-cycloserine.

7. A tolerance-inhibiting administration method for treating dementia consisting of the sequential steps of:
   (A) administering to a subject in need thereof a first-scheduled therapeutically effective dose of D-cycloserine, or a pharmacologically effective prodrug thereof;
   (B) waiting for at least 84 hours during which no additional doses of D-cycloserine, or pharmaceutically acceptable prodrug thereof, are administered to the subject; and
   (C) administering to said subject a $2^{nd}$-scheduled therapeutically effective dose of D-cycloserine or pharmacologically effective prodrug thereof one week after administrating of said first-scheduled therapeutically effective dose,
   wherein said dementia is selected from the group consisting of mild cognitive impairment, Alzheimer's Disease, vascular dementia, dementia with Lewy bodies, dementia related to Parkinson's Disease, and frontotemporal dementia; and
   wherein said D-cycloserine is administered at a dose of between about 50 mg and about 250 mg, or said pharmaceutically effective prodrug is administered as a dose of between about 90 mg and about 450 mg.

8. The method of claim 7, wherein said pharmacologically effective prodrug thereof is (R)-4-[(1-methyl-3-oxo-1-butenyl)-amino]-3-isoxazolidinone.

9. The method of claim 7, wherein said dementia is mild cognitive impairment.

10. The method of claim 7, wherein said dementia is selected from the group consisting of Alzheimer's Disease, vascular dementia, dementia with Lewy bodies, dementia related to Parkinson's Disease, and frontotemporal dementia.

11. The method of claim 7, wherein said D-cycloserine is administered on a pre-sleep basis.

12. The method of claim 7, wherein said subject is not administered an antidepressant drug compound selected from the group consisting of a selective serotonin reuptake inhibitor and a tricyclic antidepressant within one week of any of said administrations of D-cycloserine.

\* \* \* \* \*